(12) United States Patent
Lepperhoff et al.

(10) Patent No.: US 6,202,408 B1
(45) Date of Patent: Mar. 20, 2001

(54) METHOD AND APPARATUS FOR A ZERO-POINT STABILIZATION OF AN EXAUST GAS SENSOR

(75) Inventors: Gerhard Lepperhoff, Stolberg; Dietrich Meyerdierks, Aachen, both of (DE)

(73) Assignee: FEV Motorentechnik GmbH & Co., KG, Aachen (DE)

( * ) Notice: Subject to any disclaimer, the term of this patent is extended or adjusted under 35 U.S.C. 154(b) by 0 days.

(21) Appl. No.: 09/267,404

(22) Filed: Mar. 15, 1999

(30) Foreign Application Priority Data

Mar. 13, 1998  (DE) .............................. 198 10 973

(51) Int. Cl.$^7$ .................................................. F02M 25/06
(52) U.S. Cl. ........................... 60/278; 123/571; 123/568; 73/1 G; 73/118.2
(58) Field of Search ................ 60/278, 274; 123/568.15, 123/327, 568.21, 440, 198 F, 571; 73/118.1, 117.3, 1 G, 23.31, 864.81, 118.2; 204/1 T

(56) References Cited

U.S. PATENT DOCUMENTS

| | | | |
|---|---|---|---|
| 4,249,374 | * | 2/1981 | Sugasawa et al. ...................... 60/276 |
| 4,411,228 | * | 10/1983 | Sugasawa .......................... 123/198 F |
| 4,512,313 | * | 4/1985 | Tsuchida et al. ..................... 123/440 |
| 4,532,013 | | 7/1985 | Dietz et al. ............................. 73/1 G |
| 4,569,318 | * | 2/1986 | Fujimura et al. ..................... 123/327 |
| 4,590,789 | * | 5/1986 | Kunze ........................................ 73/1 |
| 4,671,107 | * | 6/1987 | Chiesa et al. ........................ 73/118.2 |
| 4,762,109 | * | 8/1988 | Jeenicke ................................ 123/571 |

FOREIGN PATENT DOCUMENTS

| | | |
|---|---|---|
| 31 26 647 | 1/1983 | (DE) . |
| 35 46 409 | 2/1987 | (DE) . |
| 39 39 166 | 5/1991 | (DE) . |
| 42 17 893 | 2/1993 | (DE) . |

\* cited by examiner

*Primary Examiner*—Thomas Denion
*Assistant Examiner*—Thai-Ba Trieu
(74) *Attorney, Agent, or Firm*—Venable; Gabor J. Kelemen

(57) ABSTRACT

An apparatus for a zero-point stabilization of an exhaust gas sensor installed in an apparatus for a thermal energy conversion of gaseous fuel while producing an exhaust gas stream, includes an arrangement for alternatingly exposing the exhaust gas sensor to a flow of exhaust gas and a flow of fresh air.

5 Claims, 3 Drawing Sheets

METHOD AND APPARATUS FOR A ZERO-POINT STABILIZATION OF AN EXAUST GAS SENSOR

CROSS REFERENCE TO RELATED APPLICATION

This application claims the priority of German Application No. 198 10 973.3 filed Mar. 13, 1998, which is incorporated herein by reference.

BACKGROUND OF THE INVENTION

For reducing the pollutant component in exhaust gases (waste gases) of internal-combustion engines and firing installations, particularly small firing devices, the composition of the exhaust gas has to be monitored and the fuel component has to be varied by suitable control devices. In internal-combustion engines additionally exhaust gas treating devices are provided. In internal-combustion engines operating with varying load requirements, particularly in internal-combustion engines for automotive vehicles, the exhaust gas treating device has to be submitted to a follow-up regulation dependent upon the load requirement and the different contents of pollutants resulting therefrom, particularly nitrogen oxides and hydrocarbons.

To perform the above-outlined regulations, exhaust gas (waste gas) sensors are provided which, however, are exposed in an environment characterized by a changing gas composition, high temperature fluctuations and also high temperature gradients. The exhaust gas sensors, however, do not remain stable, because they have a limited operating range as concerns an upper temperature limit and are also exposed to a "drift", that is, because of the changing temperature and concentration their zero-point is affected.

Several methods for calibrating measuring devices are known:

German Offenlegungsschrift (application published without examination) 42 17 893 describes a method of calibrating gas sensors for smoke gas analyses. This method uses air as the reference or calibrating gas for calibrating the measuring value for determining an $O_2$-concentration.

German Offenlegungsschrift 39 39 166 describes a calibration of sensors by using electrochemical effusion cells. Here too, the object is to set the concentration signal with the aid of a calibrating device.

In German Offenlegungsschrift 35 46 409 for the calibration of chemical sensors a calibrating gas is admitted under pressure to the sensor surrounded by the liquid to be analyzed. The calibrating gas displaces the liquid at the sensor and by capturing the pressure and temperature values at the sensor the concentration of the components of the gas to be calibrated may be determined by computation and compared with the sensor signal.

In German Offenlegungsschrift 31 26 647 a quasi-electric calibration is described in which an electric resistance is used to expand in time the calibration of the measuring instrument by calibration gases with the aid of an alignment of the constant electric resistance with the simulated measuring values.

The above-outlined known methods in all instances presuppose the existence of a measuring value or a measuring value indication, that is, a value which is above the zero-point because only in such a case can a deviation be determined. The "wandering" or "drifting" of the zero point cannot be determined with the known methods and thus can also not be taken into account in a regulating device.

It is further feasible to detect the drift and also to achieve a stability of indication by taking into account the changing influences with the aid of different algorithms in the software of the regulating device. For such a proceeding, however, an independent reference system is not available which also has a certain stability as concerns aging.

SUMMARY OF THE INVENTION

It is an object of the invention to provide an improved apparatus of the above-outlined type by means of which the drift of an exhaust gas sensor may be compensated for and also, in case of high waste (exhaust) gas temperatures, the working temperature range of the exhaust gas sensor may be maintained.

This object and others to become apparent as the specification progresses, are accomplished by the invention, according to which, briefly stated, the apparatus for a zero-point stabilization of an exhaust gas sensor installed in an apparatus for a thermal energy conversion of gaseous fuel while producing an exhaust gas stream, includes an arrangement for alternatingly exposing the exhaust gas sensor to a flow of exhaust gas and a flow of fresh air.

By virtue of the arrangement as outlined above, a reference system is provided for the exhaust gas sensor, since it is repeatedly exposed all around to fresh air so that, accordingly, in such operational phases the same initial value, that is, the "zero point" is necessarily indicated. By virtue of aging effects, temperature effects and the like, the signal which is considered to be the zero point signal may change, that is, it may drift, and thus the invention provides the possibility for the regulating device to detect such a drift during the phases of the fresh air exposure by a comparison with a predetermined value and then to correct such value by the regulating device. Thus, the arrangement provides for the possibility to continuously restore the regulating device to the zero point even during the operation of the exhaust gas sensor. The invention further provides that at a given temperature of the fresh air, for example, at an environmental temperature, the exhaust gas sensor is cooled and, corresponding to the temperature difference, may be maintained within its operating temperature range.

The term "apparatus for converting thermal energy" in the meaning of the present invention also encompasses firing systems, particularly small firing devices in addition to combustion engines, particularly piston-type engines. The term "gaseous fuels" encompasses fuels which are initially in gaseous form as they are used for small firing devices, as well as liquid fuels which are atomized and/or vaporized in preparation for the energy conversion.

According to an advantageous feature of the invention, the alternation between exhaust gas exposure and fresh gas exposure is effected by a controllable valve assembly. This arrangement makes possible to control the duration and the alternating frequency of the exhaust gas exposure and the fresh air exposure dependent on the mode of use and as a function of the changing load conditions. Thus, in small firing devices which have essentially a constant fuel flow rate during the operating period, the sensor needs to be only infrequently exposed to the fresh air flow. The method may be coupled with the regulating device in such a manner that an alternation between the exposure to exhaust gas and the exposure to fresh gas is effected only when the fuel is actually combusted. In contrast, in an internal-combustion engine, particularly in an engine for an automotive vehicle which has varying load requirements and therefore varying components of pollutants in the exhaust gas and, last but not least, because of the substantially higher exhaust gas temperature, a frequent alternation between an exposure to the exhaust gas and an exposure to the fresh air has to be performed. In this manner, it is not only ensured that by means of the exhaust gas sensor the after-connected regulating device always receives the "actual" exhaust gas data but also, during the period of exposure to fresh air, a cooling of the exhaust gas sensor is achieved so that the latter may be held in its operating temperature range.

According to a further advantageous feature of the invention, the exhaust gas sensor is exposed to an exhaust gas flow which is branched off the main exhaust gas stream. This measure which also results in small flow cross sections in the exposure region for the exhaust gas sensor, ensures not only a superior flow pattern in the contact region with the exhaust gas sensor but the partial stream may be taken out from a core zone of the main exhaust gas stream so that external interferences are excluded to a substantial extent. While in principle it is possible to introduce the fresh air into the exposure zone of the exhaust gas sensor by an additional fan, according to a further advantageous feature of the invention the fresh air is introduced to the exhaust gas sensor by utilizing a pressure drop generated in the exhaust gas flow. Such a procedure is particularly expedient in small firing devices because a sufficient vacuum with respect to the environmental air is present in the outlet flue so that the fresh air is drawn into the exposure zone of the exhaust gas sensor by the vacuum in the flue.

In accordance with yet another advantageous feature of the invention which finds application in an internal-combustion engine, particularly in a piston-type engine which constitutes an apparatus for a thermal energy conversion, the engine conventionally has intake and exhaust manifolds. In this arrangement the exhaust gas sensor is periodically exposed to the partial exhaust gas stream branched off the exhaust manifold and to a fresh air stream taken from the environment and the two gas streams are alternatingly introduced into the intake manifold. Such an arrangement, for supplying both the partial exhaust gas stream and the fresh air stream, advantageously utilizes the generated pressure drop between the exhaust gas conduit which has an excess pressure and the intake conduit which, as compared to the environmental air, is under vacuum.

In all modes of application it is feasible according to the invention to couple the controllable valve with a setting drive which is, in turn, controlled by a regulating or control device. It is, however, expedient to control the valve independently by an alternating, particularly pulsating, gas pressure in the exhaust gas conduit. Such a use is particularly advantageous in piston-type internal-combustion engines because there a pulsating exhaust gas flow is present in any event which may be utilized for operating the valve which switches between exhaust gas and fresh air admission to the exhaust gas sensor. The pressure wave opens the flow of the exhaust gas and at the same time closes the flow of fresh air whereas the vacuum wave closes the flow of the exhaust gas and, at the same time, opens the flow of the fresh air. In this manner an alternating exposure of the exhaust gas sensor to exhaust gas and fresh air is achieved and also, the exhaust gas sensor is maintained at an average operating temperature.

The invention further relates to an apparatus for the zero-point stabilization of an exhaust gas sensor of a regulating device for reducing the pollutant component in exhaust gases of a device for converting thermal energy of gaseous fuels. The apparatus has at least one exhaust gas conduit, particularly for practicing the invention. Thus, according to the invention, the exhaust gas conduit is provided with a branch conduit which has an exhaust gas inlet and a fresh air inlet and in which an exhaust gas sensor is arranged downstream of the gas inlets as viewed in the flow direction of the gases. Further, in the merging region of the gas inlets a valve is disposed by means of which the two gas intakes may be alternatingly opened and closed. Such a basic form of the invention may find application, for example, in small firing devices and may be disposed directly in the exhaust gas conduit (flue) region because the draft in the flue is sufficient to draw air into the branch conduit from the environment when the fresh air inlet is opened.

According to an advantageous feature of the apparatus, in a device for converting thermal energy, constituted by an internal-combustion engine with an intake manifold and an exhaust manifold, the branch conduit is formed by a connecting conduit between the exhaust and intake manifolds, and further, the exhaust gas sensor is disposed in the connecting conduit. In this arrangement too, it is possible to utilize, without additional conveying devices for the partial exhaust gas flow and/or the fresh air flow, the natural pressure drop between the exhaust manifold and the intake manifold for advancing both the partial exhaust gas stream and the fresh air stream.

In both modes of application, the valve device may be formed by a controllable valve provided with a setting drive.

In accordance with a further feature of the apparatus of the invention, particularly for use in piston-type internal-combustion engines, the valve arrangement is provided in a work chamber which is connected to the exhaust manifold and the intake manifold by respective connecting conduits. Further, the work chamber has a fresh air inlet. A valve which is disposed in the work chamber and which is operated, for example, by a double-acting electromagnetic actuator, alternatingly opens and closes the exhaust gas inlet and the fresh air inlet.

In accordance with a further feature of the apparatus of the invention, particularly for use in piston-type internal-combustion engines, a valve arrangement is provided which has a valve diaphragm subdividing the work chamber into an exhaust gas chamber and a fresh air chamber. The valve diaphragm periodically closes the fresh air intake opening as urged by the pulsating exhaust gas stream. Further, between the exhaust gas chamber and the fresh air chamber a check valve is disposed which too, is opened and closed by pressure fluctuations and which, when open, allows exhaust gas to flow from the exhaust gas chamber into the fresh air chamber.

DESCRIPTION OF THE PREFERRED EMBODIMENTS

Figure 1:
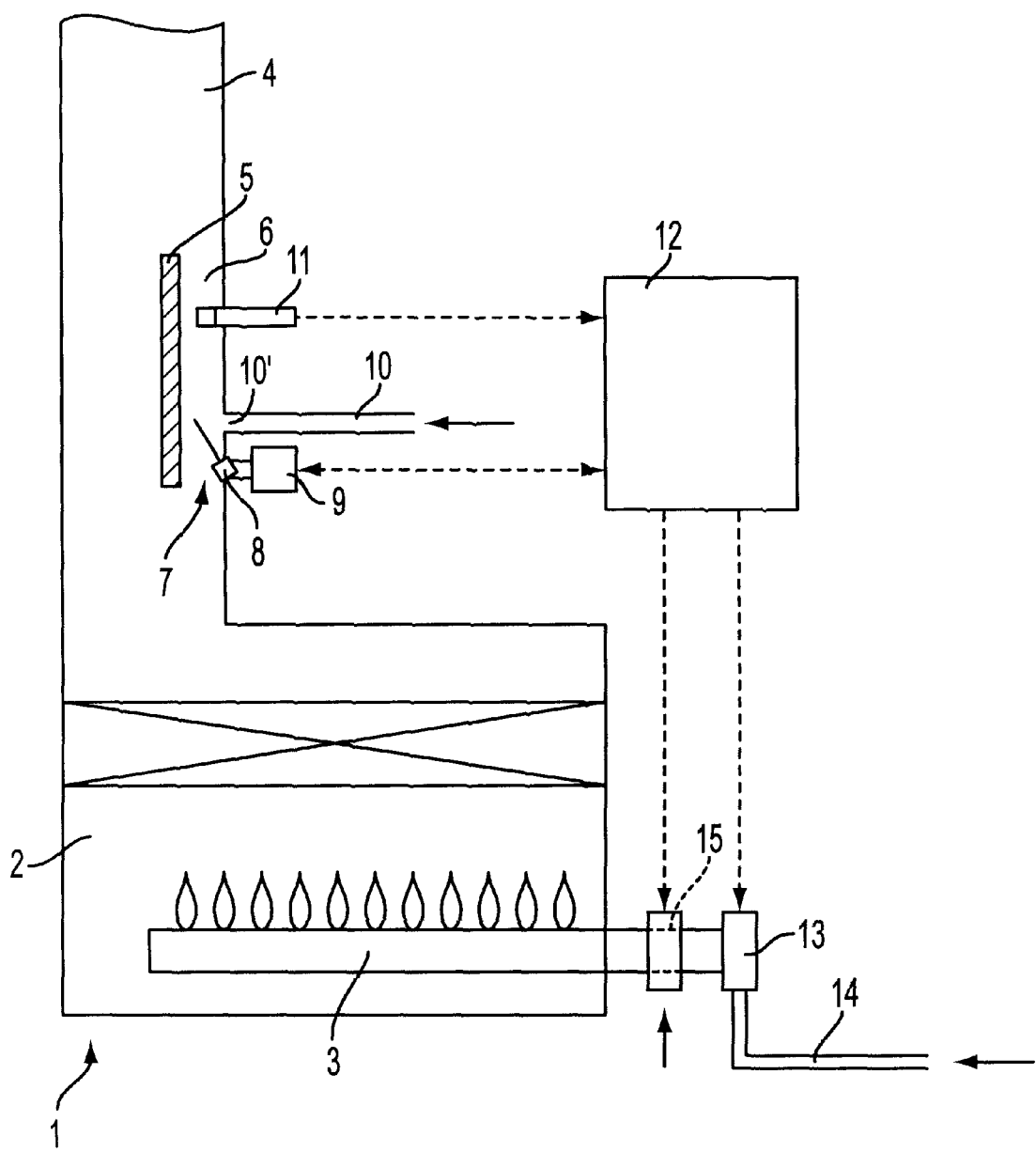
FIG. 1 is a schematic elevational view of a small firing device incorporating the invention.

FIG. 1 illustrates a small firing device, for example, a gas heater having a furnace 1 which includes a firing chamber 2 accommodating an atmospheric burner 3. The exhaust gases are removed from the firing chamber 2 through a flue 4.

In the flue 4 a partition 5 defines, with the flue wall, a branch conduit 6 having an inlet 7. A pivotally mounted valve (valve flap) 8 which is disposed at the inlet 7, may be actuated by a setting device 9. By means of the valve assembly 8 the inlet 7 may be shut off to prevent any exhaust gas flow through the branch conduit 6.

A fresh air conduit 10 opens into the branch conduit 6 close to the inlet 7 thereof. The opening 10' of the fresh air conduit 10 may be closed by the flap valve 8 assembly 8 in one of its positions.

An exhaust gas sensor 11 is positioned in the branch conduit 6 downstream of the inlet 7 and the opening 10' of the fresh air conduit 10 as viewed in the flow direction of the exhaust gases in the branch conduit 6.

The exhaust gas sensor may be, for example, an oxide component sensor, by means of which gas components that need to be reduced or oxidized are detected. Instead of such a multiple sensor it is feasible to use separate sensors for the gas components which are to be reduced and those which are to be oxidized.

The heating device 1 is provided with a regulating device 12 by means of which, dependent on requirements of heat consumption, the gas supply to the burner 3 may be varied, for example, by a valve 13 provided in the gas conduit 14. Further, by means of a setting device 15, the regulating device 12 may affect the supply of primary air and secondary air to the burner 3, dependent upon signals from the exhaust gas sensor 11 which too, is coupled to the regulating device 12.

The regulating device 12 may actuate the valve 8, for example, by a clocked signal so that after a longer open period for the partial exhaust gas stream and during a simultaneous closed state of the fresh air conduit 10, the exposure of the exhaust gas sensor 11 to the exhaust gas flow is discontinued, and for a predetermined, shorter period the exhaust gas sensor 11 is exposed to fresh air as the valve 8 opens the fresh air conduit 10. The signal emitted by the exhaust gas sensor 11 during the phase when the latter is exposed to fresh air is compared in the regulating device 12 with a predetermined desired value. Since because of drifting phenomena, for example, aging, a signal deviation may be determined, the regulating device 12 automatically performs a corresponding "zero-point correction". At the same time, the regulating device 12 expediently ensures that the exposure to fresh air occurs only when the burner 3 is in operation to thereby provide for the zero-point calibration such that immediately prior to the exposure to fresh air, the exhaust gas sensor 11 has been exposed to a flow of exhaust gas.

Figure 2:
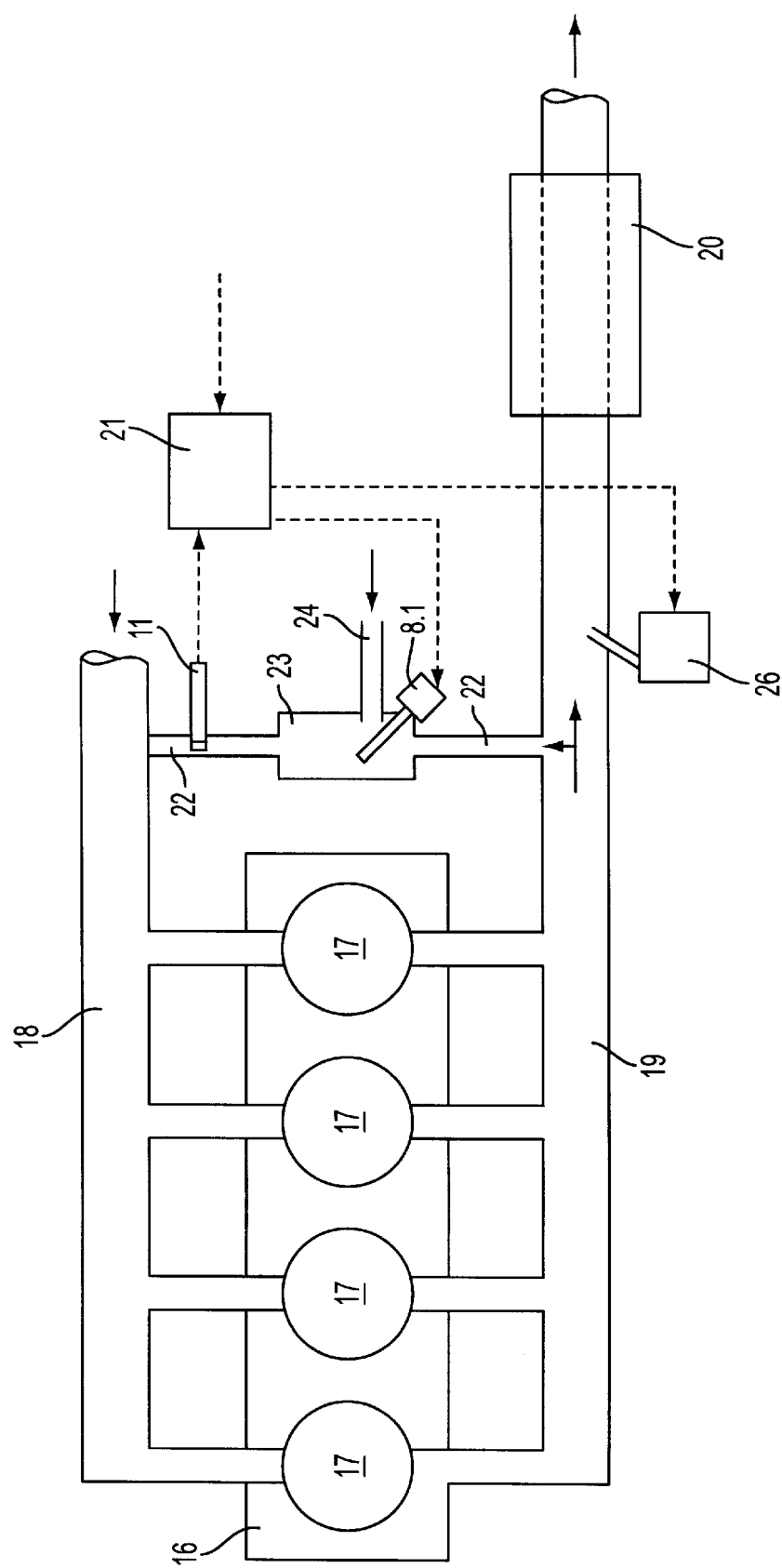
FIG. 2 is a schematic top plan view of an internal-combustion engine incorporating the invention.

If, for example, as described above, an atmospheric burner is used in a firing device, then during periods when the burner 3 is inoperative, at which time for safety reasons air is directed into the exhaust gas conduit such as the flue 4, such an air flow may be utilized for the zero-point stabilization. It is to be understood, however, that the invention may find application in firing devices which operate with heaters other than an atmospheric burner. Turning to FIG. 2, the invention may find advantageous use, for example, in a piston-type internal-combustion engine, whose four cylinders 17 are coupled with an intake manifold 18 and an exhaust manifold 19. In the exhaust manifold 19 an exhaust gas treating device 20 is disposed which may have, for example, a reducing and/or an oxidizing exhaust gas treating component.

The engine 16 is coupled with an engine control unit 21 which, based on load requirements, regulates and controls in a conventional manner the various engine functions such as ignition, fuel supply (fuel injection), etc. In an engine of such a type an exhaust sensor is to be disposed in the exhaust manifold 19. This, however, involves the problem that the exhaust gases of an internal-combustion engine have a very elevated temperature and further, the conventional exhaust gas sensors have working temperatures which lie below the exhaust gas temperatures. Consequently, heretofore only the air component in the exhaust gas could be detected by means of a lambda sonde. The signals of the exhaust gas sensors are to serve for controlling the exhaust gas emission by means of the engine control unit 21 in such a manner that during exhaust gas treatment by means of storage catalysts the emissions behind the catalysts 20 are measured by an exhaust gas sensor 11. If the concentrations exceed a critical value, the regeneration of the storage catalyst is effected by enriching the mixture.

FIG. 2 illustrates an arrangement in which, for example, for reducing the nitrogen oxide component, suitable reduction agents are added to the exhaust gas by a metering device 26, or by regulating the exhaust gas composition by means of the engine control unit 21, an $HC/No_x$ ratio is set that is required for an $No_x$ reduction. For this purpose, the exhaust gas sensor 11, together with the connecting conduit 22 is to be disposed upstream of the exhaust gas treating device 20 as viewed in the direction of gas flow. In case of an engine regulation or a regulation of the exhaust gas treating device by the engine control unit 21 such that the concentration of the exhaust gas composition is affected by the addition of reduction agents, for example, in case of storage catalysts, the connecting conduit 22 is to be coupled to the exhaust pipe downstream of the exhaust gas treating device 20.

Thus, according to the invention, between the exhaust manifold 19 and the intake manifold 18 a connecting conduit 22 (branch conduit) is disposed; it branches off as close as possible behind the exhaust port of the last cylinder 17 as seen in the flow direction of the exhaust gases or it is branched off downstream of the exhaust gas treating device 20. For improving the signal emission of the exhaust gas sensor 11, the latter is arranged, together with the work chamber 23 and the fresh air intake conduit 24, directly on the exhaust manifold 19.

The connecting conduit 22 is interrupted by the work chamber (switching chamber) 23 which thus communicates with the intake and exhaust manifolds 18 and 19 and into which also merges a fresh air conduit 24. By means of a controllable valve 8.1 exhaust gas and fresh air may be alternatingly introduced into the work chamber 23 in which the pressure difference between the pulsating exhaust gas flow in the exhaust manifold 19 and the relatively slight vacuum in the air intake manifold 18 is sufficient to allow exhaust gas from the exhaust manifold 19 as well as fresh air from the fresh air conduit 24 to flow into the intake manifold 18 via the work chamber 23. The position of the valve 8.1 determines the periods during which exhaust gas or fresh air is introduced into the work chamber 23.

The exhaust gas sensor 11 is positioned in the connecting conduit 22 downstream of the work chamber 23 as viewed in the flow direction of the gases. The exhaust gas sensor 11 is coupled to a regulating device which, for example, may be a component of the engine control unit 21 and which may perform a determination of the "zero-point" for the exhaust gas sensor 11 during exposure to fresh air and a determination of the exhaust gas composition during exposure to the exhaust gas. Dependent on the gas composition, an introduction of reducing substances via a corresponding supply device 26 into the exhaust manifold 19 upstream of the exhaust gas treating device 20 may be effected by suitable regulation. Or, as an alternative, a suitable regulation may be performed via the engine control unit 21.

Since the exhaust gas sensor 11 is repeatedly exposed to relatively cool fresh air, at the exhaust gas sensor 11 a temperature will be set which is below the exhaust gas temperature and thus the exhaust gas sensor 11 may be maintained at its working temperature range.

Figure 3:
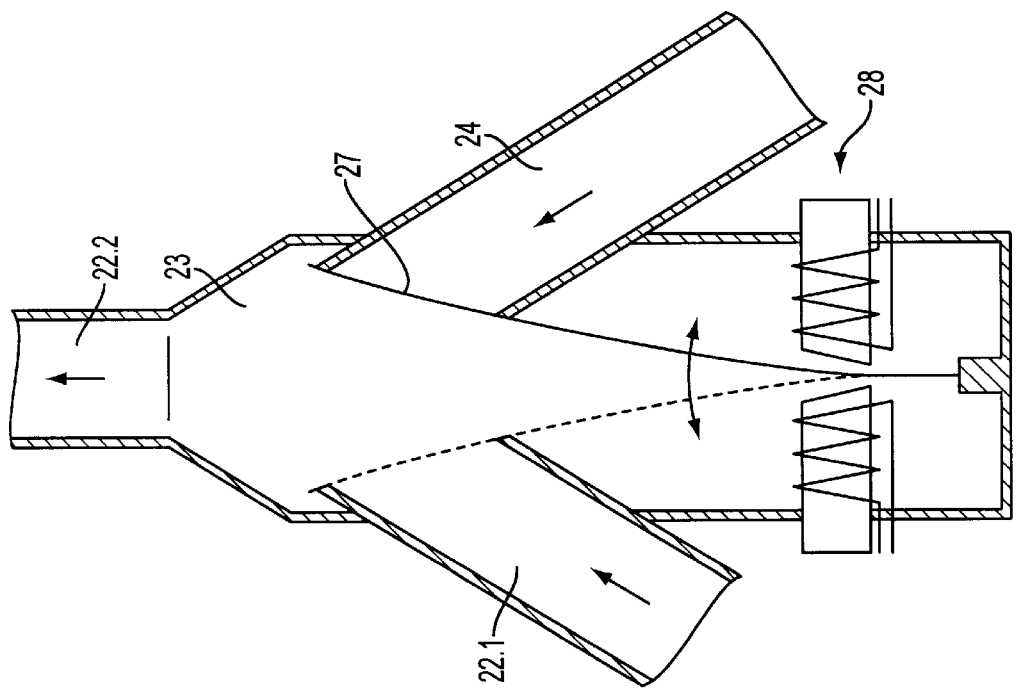
FIG. 3 is a schematic sectional elevational view of a valve assembly with valve drive, forming part of the invention.

FIG. 3 illustrates an embodiment of the work chamber (switching chamber) 23. The work chamber 23 communicates with the fresh air intake conduit 24 as well as with the exhaust manifold 19 by the connecting conduit part 22.1 and with the intake manifold 18 by the connecting conduit part 22.2. The opening of the connecting conduit part 22.1 as well the opening of the air intake conduit 24 face one another so that by means of a spring-biased valve flap 27 which may be moved back and forth, for example, by a controlled electromagnetic actuator 28, the exhaust gas conduit part 22.1 and the fresh air conduit 24 may be alternatingly opened and closed. The gas stream entering in each instance the work chamber 23 flows across the exhaust gas sensor 11 (not visible in FIG. 3) via the connecting conduit portion 22.2. The control of the electromagnetic actuator 28 may be effected, for example, by the engine control unit 21.

Figure 4:
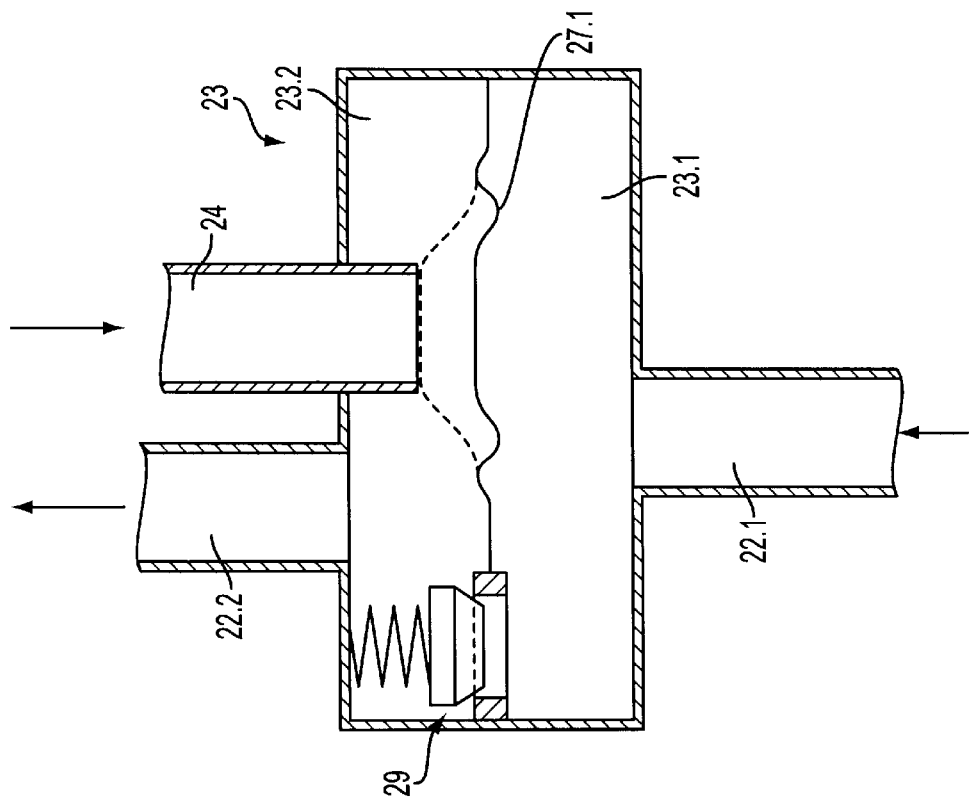
FIG. 4 is a schematic sectional elevational view of a valve arrangement driven by the fluctuation of an exhaust gas flow according to the invention.

FIG. 4 illustrates an automatically operating valve assembly. In this embodiment too, a work chamber 23 is provided which is subdivided by a valve diaphragm 27.1 into an exhaust gas chamber 23.1 and a fresh air chamber 23.2. In the exhaust chamber 23.1 merges that portion 22.1 of the connecting conduit 22 which is coupled with the exhaust manifold 19 while the air intake conduit 24 merges into the fresh air chamber 23.2. The fresh air chamber 23.2 further communicates with that portion 22.2 of the connecting conduit 22 which is coupled to the intake manifold 18. In the work chamber 23 a check valve 29 is arranged which is set in such a manner that it opens upon the maximum pressure in the pulsating exhaust gas flow. As a result, exhaust gas may flow into the fresh air chamber 23.2 from the exhaust gas chamber 23.1.

The valve diaphragm 27.1 is configured such that when the exhaust gas flow attains a positive pressure in the exhaust gas chamber 23.1, it closes the fresh air conduit 24, while, at the same time, the check valve 29 opens in response to such a pressure and thus allows exhaust gas to flow from the exhaust gas chamber 23.1 through the fresh air chamber 23.2 into the connecting conduit part 22.2 coupled to the air ID intake manifold 18. The positive intake gas pressure impulse which closes the air intake conduit 24 is followed by a vacuum wave in the exhaust gas manifold 19 which allows the valve diaphragm 27.1 to snap back into its original position by its own resilience so that the air intake conduit 24 is opened and the check valve 29 is closed. As a result, based on the pressure difference between the environmental air and the air intake manifold 18, fresh air may flow through the air chamber 23.2 into the branch conduit part 22.2.

In both embodiments of FIGS. 3 and 4 the exhaust gas sensor 11 is arranged in that portion 22.2 of the connecting conduit 22 which leads to the air intake manifold 18. The components of the system may be spatially also arranged in such a manner that at least the portion 22.2 of the connecting conduit 22 lies in a coolant air stream so that in addition to directly exposing the exhaust gas sensor 11 to fresh air, the surrounding environment of the exhaust gas sensor 11 is also cooled and thus the temperature level in the immediate region of the exhaust gas sensor 11 may be maintained at a low value.

It will be understood that the above description of the present invention is susceptible to various modifications, changes and adaptations, and the same are intended to be comprehended within the meaning and range of equivalents of the appended claims.

What is claimed is:

1. An apparatus for a thermal energy conversion by a gaseous fuel, comprising
   (a) an exhaust gas conduit through which exhaust gases produced by the combustion of fuel pass;
   (b) a branch conduit having
      (1) a first inlet communicating with said exhaust gas conduit for introducing exhaust gas into said branch conduit;
      (2) a second inlet for introducing fresh air into said branch conduit; and
      (3) an outlet through which gases exit said branch conduit; and
   (c) a regulating device for reducing pollutant components in the exhaust gas; said regulating device including
      (1) an exhaust gas sensor disposed in said branch conduit downstream of said first and second inlets as viewed in a direction of gas flow in said branch conduit toward said outlet;
      (2) a valve movable into a first position in which said valve maintains open said first inlet and maintains closed said second inlet and a second position in which said valve maintains open said second inlet and maintains closed said first inlet; and
      (3) operating means for periodically moving said valve into said first and into said second position for alternatingly exposing said exhaust sensor to a flow of exhaust gas and to a flow of fresh air for effecting a zero-point stabilization of said exhaust gas sensor.

2. The apparatus as defined in claim 1, wherein said apparatus is an internal-combustion engine including an intake manifold and an exhaust manifold; further wherein said branch conduit is a connecting conduit; said first inlet communicating with said exhaust manifold and said outlet communicating with said intake manifold.

3. The apparatus as defined in claim 2, further comprising an engine control unit including said regulating device; said operating means being connected to said engine control unit; said connecting conduit being composed of
   (a) a first connecting conduit part having a first end coupled to said exhaust manifold and a second end;
   (b) a second connecting conduit part having a first end coupled to said intake manifold and a second end; and
   (c) a work chamber coupled to said second end of said first connecting conduit part and to said second end of said second connecting conduit part; said second end of said first connecting conduit part constituting said first inlet; said second inlet merging into said work chamber.

4. The apparatus as defined in claim 3, wherein said exhaust gas sensor is disposed in said second connecting conduit part.

5. The apparatus as defined in claim 2, said connecting conduit being composed of
   (a) a first connecting conduit part having a first end coupled to said exhaust manifold and a second end;

(b) a second connecting conduit part having a first end coupled to said intake manifold and a second end; and (c) a work chamber coupled to said second end of said first connecting conduit part and to said second end of said second connecting conduit part; said second inlet merging into said work chamber; and said valve being composed of (a) a diaphragm dividing said work chamber into an exhaust gas chamber being in communication with said second end of said first connecting conduit part and a fresh air chamber being in communication with said second end of said second connecting conduit part and with said second inlet; said diaphragm being movable by a fluctuating pressure in said exhaust gas chamber between first and second positions; in said first position of said diaphragm said second inlet being maintained closed and in said second position of said diaphragm said second inlet being maintained open; and (b) a check valve providing a one-way communication through said first inlet between said exhaust gas chamber and said fresh air chamber; said check valve being movable by a fluctuating pressure in said exhaust gas chamber between first and second positions; in said first position of said check valve said first inlet being maintained open allowing a flow of exhaust gas from said exhaust gas chamber into said fresh air chamber and in said second position of said check valve said first inlet being maintained closed.

* * * * *

UNITED STATES PATENT AND TRADEMARK OFFICE
CERTIFICATE OF CORRECTION

PATENT NO.    : 6,202,408 B1                                          Page 1 of 1
DATED         : March 20, 2001
INVENTOR(S)   : Gerhard Lepperhoff et al.

It is certified that error appears in the above-identified patent and that said Letters Patent is hereby corrected as shown below:

Title page, Item [54],
The title should read: -- APPARATUS FOR A ZERO POINT STABILIZATION OF AN EXHAUST GAS SENSOR --.

Signed and Sealed this

Fourteenth Day of August, 2001

Attest:

NICHOLAS P. GODICI
Attesting Officer    Acting Director of the United States Patent and Trademark Office